United States Patent [19]

Kohayakawa

[11] Patent Number: 5,757,463
[45] Date of Patent: May 26, 1998

[54] EYE EXAMINING APPARATUS SCANNING THE EYE WITH A LIGHT BEAM

[75] Inventor: Yoshimi Kohayakawa, Yokohama, Japan

[73] Assignee: Canon Kabushiki Kaisha, Tokyo, Japan

[21] Appl. No.: 941,193

[22] Filed: Sep. 30, 1997

Related U.S. Application Data

[63] Continuation of Ser. No. 651,510, May 22, 1996, abandoned, which is a continuation of Ser. No. 264,505, Jun. 23, 1994, abandoned.

[30] Foreign Application Priority Data

Jun. 29, 1993 [JP] Japan ..................... 5-185597

[51] Int. Cl.$^6$ ........................................ A61B 3/10
[52] U.S. Cl. ........................... 351/214; 351/221
[58] Field of Search ............................ 351/206, 208, 351/209, 210, 211, 221, 214; 354/62

[56] References Cited

U.S. PATENT DOCUMENTS

| | | | |
|---|---|---|---|
| 4,609,287 | 9/1986 | Kohayakawa | 356/124 |
| 4,697,895 | 10/1987 | Sekiguchi et al. | 351/243 |
| 4,704,012 | 11/1987 | Kohayakawa et al. | 350/516 |
| 4,820,037 | 4/1989 | Kohayakawa et al. | 351/211 |
| 4,830,483 | 5/1989 | Kohayakawa et al. | 351/221 |
| 4,854,692 | 8/1989 | Kobayashi | 351/206 |
| 4,950,070 | 8/1990 | Aizu et al. | 351/206 |
| 4,991,953 | 2/1991 | Pflibsen et al. | 351/214 |
| 5,037,194 | 8/1991 | Kohayakawa et al. | 351/224 |
| 5,094,523 | 3/1992 | Reznichenko et al. | 351/221 |
| 5,144,346 | 9/1992 | Nakamura et al. | 351/208 |
| 5,231,430 | 7/1993 | Kohayakawa | 351/243 |
| 5,231,460 | 7/1993 | Kohayakawa | 356/126 |
| 5,237,351 | 8/1993 | Kohayakawa et al. | 351/243 |
| 5,249,003 | 9/1993 | Kohayakawa | 351/211 |
| 5,280,313 | 1/1994 | Kohayakawa | 351/211 |
| 5,325,134 | 6/1994 | Kohayakawa | 351/212 |

*Primary Examiner*—Hung X. Dang
*Attorney, Agent, or Firm*—Fitzpatrick, Cella, Harper & Scinto

[57] ABSTRACT

An eye examining apparatus has a light source generating a beam of light to be applied to an eye to be examined, and a photoelectric sensor for receiving the light from the eye to be examined. The examination of the eye to be examined is executed by the light reception of the photoelectric sensor. The apparatus further includes a scanning optical system for deflecting the beam of light to be applied from the light source to the eye to be examined and executing the scanning of the eye to be examined by the beam of light to be applied. The scanning optical system directs the light from the scanned position of the eye to be examined to the photoelectric sensor. The apparatus also includes an observation system for the eye to be examined for displaying an area wider than the scanned region of the eye to be examined by the use of the light passed through a portion of a member the scanning optical system.

15 Claims, 5 Drawing Sheets

FIG. 10

EYE EXAMINING APPARATUS SCANNING THE EYE WITH A LIGHT BEAM

This application is a continuation of application Ser. No. 08/651,510, filed May 22, 1996, now abandoned, which is a continuation of application Ser. No. 08/264,505, filed Jun. 23, 1994, abandoned.

BACKGROUND OF THE INVENTION

1. Field of the Invention

This invention relates to an eye examining apparatus for use during ophthalmic diagnosis in ophthalmic hospitals or the like.

2. Related Background Art

Ophthalmoscopes, slit lamps, flare cell meters, eye fundus cameras, etc. have heretofore been used as apparatuses for observing or examining the interior of the cornea of an eye to be examined. For example, the slit lamp is utilized as an eye examining apparatus for applying a beam of slit light to a transparent body such as a cornea or a crystalline lens from an oblique direction to thereby effect the observation of the endothelia or the examination of mixing foreign substances by light section. Also, the eye fundus camera is utilized as an eye examining apparatus for separating illuminating light and received light with a fixed apertured mirror, and receiving the light with a CCD sensor or the like to thereby observe or photograph the condition of the surface of the cornea or the fundus of the eye.

Among such apparatuses, an apparatus for receiving reflected light from the eye to be examined to thereby effect the photographing of the eye to be examined is known as an apparatus which can obtain photographed images of good contrast.

SUMMARY OF THE INVENTION

In view of the above-described examples of the prior art, the present invention has as its first object the provision of an eye examining apparatus of the light beam scanning type which is simplified in construction and can be made more compact.

Other objects of the present invention will become apparent from the following detailed description of some embodiments of the invention.

DESCRIPTION OF THE PREFERRED EMBODIMENTS

The invention will hereinafter be described with respect to some embodiments thereof shown in the drawings.

Figure 1:
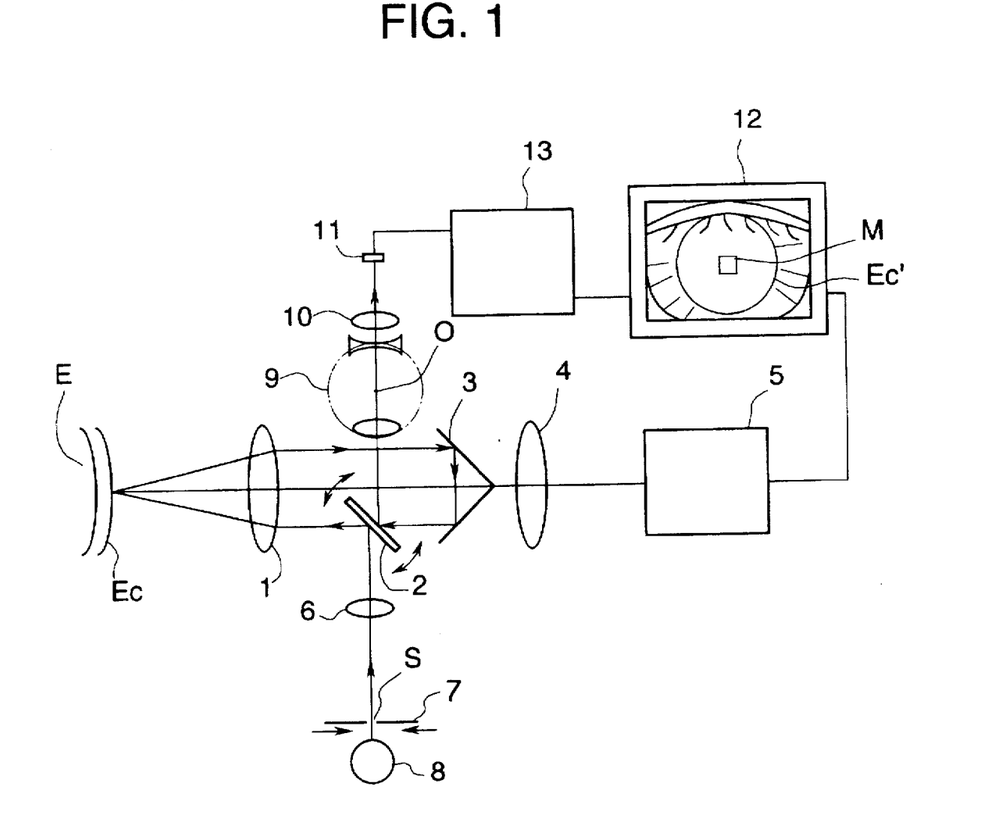
FIG. 1 shows the construction of a first embodiment of the present invention.

FIG. 1 shows the construction of a first embodiment of the present invention. An objective lens 1, a vibrating mirror 2 disposed on one side of an optical axis, a compound mirror 3, a lens 4 and a television camera 5 are arranged ahead of an eye E to be examined. The compound mirror 3 is formed into an L-shape by two mirrors, and is disposed at a position at which the linear of intersection between the two mirrors intersects the optical axis. The vibratory mirror 2 and the compound mirror 3 each is a transparent optical member of glass or like material having applied to its surface a dichroic film for reflecting a wavelength of a beam of light from a light source 8.

Figure 2:
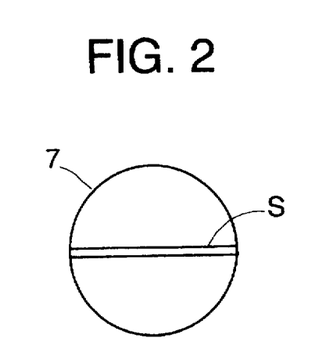
FIG. 2 is a front view of a slit plate.
Figure 3:
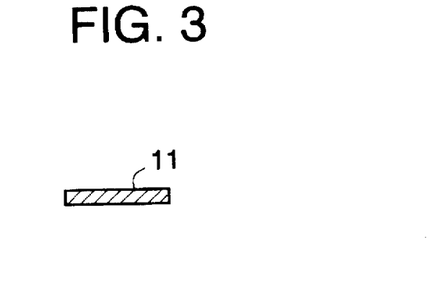
FIG. 3 is a front view of a linear array sensor.

An illuminating optical system is disposed in one direction of reflection orthogonal to the aforementioned optical axis relative to the vibrating mirror 2, and a light receiving optical system is disposed in the other direction of reflection. The illuminating optical system comprises a lens 6, a slit plate 7 having a variable width slit S as shown in FIG. 2, and a light source 8, and the light receiving optical system comprises a variable power lens 9, an imaging lens 10 and a linear array sensor 11 as shown in FIG. 3. The variable power lens 9 is rotatable about the center point 0 thereof, whereby the magnification thereof is changed in three stages and when the magnification thereof is changed, the width of the slit S of the slit plate 7 is varied in response thereto. The slit S of the slit plate 7 and the linear array sensor 11 are in conjugate relationship with each other, and even when the vibratory mirror 2 vibrates, this conjugate relationship is always maintained, whereby a so-called cofocal system is constituted.

The output of the television camera 5 is connected to a television monitor 12, and the output of the linear array sensor 11 is connected to the television monitor 12 through a signal processor 13.

A beam of light from the light source 8 impinges on one surface of the vibrating mirror 2 via the slit plate 7 and the lens 6. Since the vibrating mirror 2 is disposed at a location which deviates toward one side of the optical axis, the beam of light reflected by the vibrating mirror 2 passes through one side of the objective lens 1 and illuminates the cornea Ec of the eye E to be examined. The vibrating mirror 2 vibrates about its central portion as indicated by arrows and therefore, the slit beam of light scans the cornea Ec.

The reflected light from the cornea Ec passes through the other side of the objective lens 1, is reflected by the two surfaces of the compound mirror 3, is further reflected by the back of the vibrating mirror 2 and is imaged on the linear array sensor 11 by the variable power lens 9 and the imaging lens 10.

To enable the anterior part of the eye E to be examined to be observed, a light source, not shown, emits a beam of light in another wavelength range and illuminates the anterior eye part, and the reflected light therefrom is transmitted through a vibrating mirror 2 designed to transmit this wavelength therethrough and the compound mirror 3, and is imaged on the television camera 5 by the lens 4, and a cornea image Ec' is displayed on the television monitor 12. If in this case, the apparatus is designed so that the reflected light becomes a parallel beam of light between the objective lens 1 and the lens 4, any vibration of the vibrating mirror 2 will not affect the imaging system.

Also, an index mark M made by a symbol generating circuit in the signal processor 13 is displayed on the television monitor 12, and this index mark M indicates an area being observed by a scanning system. The signal from the linear array sensor 11 is processed by the signal processor 13, and the image thereof is changed over with the cornea image Ec' from the television camera 5 and is enlarged and displayed on the television monitor 12.

Figure 4:
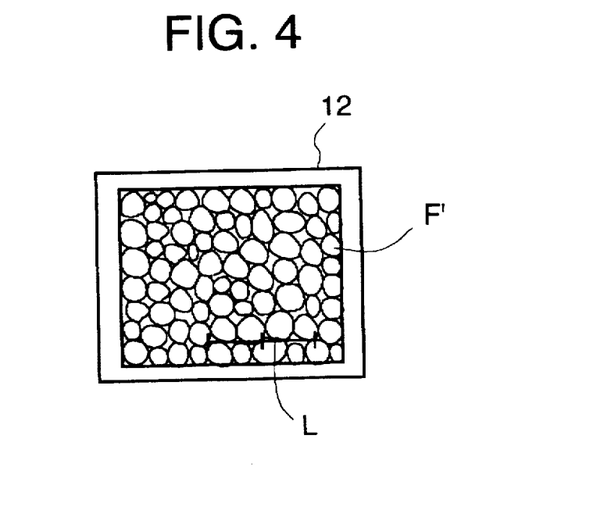
FIG. 4 is a front view of a television monitor displaying endothelia.

FIG. 4 shows the image F' of corneal endothelium enlarged and displayed on the television monitor 12 in this manner, and likewise a scale L made in the symbol generating circuit is also displayed on the television monitor.

The image F' of corneal endothelium corresponding to a location on the cornea image Ec' can be understood from the above-described two images and therefore, a detailed diagnosis of symptoms becomes possible. Further, since the slit S of the slit plate 7 and the linear array sensor 11 together constitute a cofocal system, the mixing of the reflected light from the surface of the cornea Ec or the like can be prevented and noise or stray light resulting from the background light can also be avoided and thus, it becomes unnecessary to operate the apparatus in a darkroom.

When the turbidity in an anterior chamber of the eye is to be observed and measured, the anterior part of the eye is first displayed on the television monitor by the use of an anterior eye part observation systems to thereby effect alignment, whereafter the screen is changed over and observation and measurement are effected by the use of a scanning optical system. Thus, observation and measurement becomes possible by scattered reflected light from cells or the like floating in the anterior chamber of the eye and therefore, if this signal is analyzed, the quantitative analysis of the degree of turbidity or the like will become possible. When the observation of the anterior eye part is not effected, similar measurement is possible by the use of not dichroic mirrors but total reflection mirrors as the vibrating mirror 2 and the compound mirror 3.

In lieu of the slit plate 7, a variable power lens 9' equal to that in the light receiving optical system can also be used in the illuminating optical system to effect measurement. Also, a prism can be used in place of the compound mirror 3. Again in this case, the optical axis of the beam of reflected light from the cornea Ec reflected by the vibratory mirror 2 and the optical axis of the beam of light from the illuminating light source 8 transmitted through the vibrating mirror 2 somewhat deviate from each other and therefore, only the beam of measuring light can be projected onto the linear array sensor 11.

Figure 5:
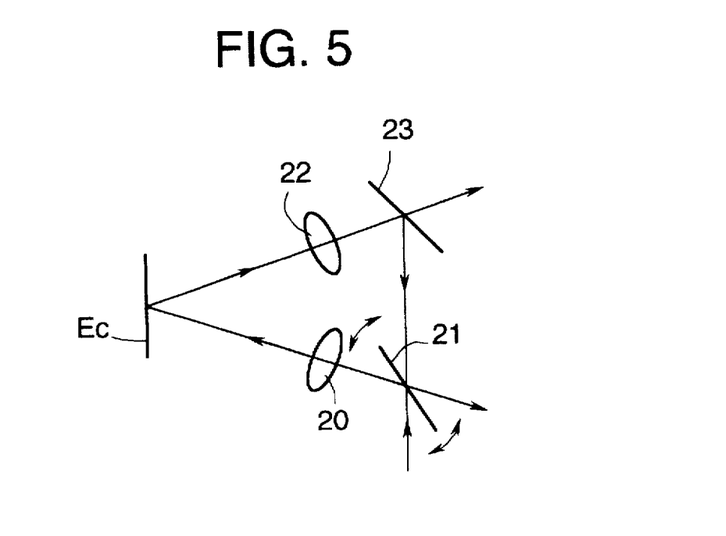
FIG. 5 shows the construction of a second embodiment of the present invention.

FIG. 5 shows the construction of a scanning optical system in a second embodiment of the present invention. The optical axis of incident light and the optical axis of reflected light are provided in oblique directions ahead of the cornea Ec of the eye E to be examined, a lens 20 and a vibrating mirror 21 are disposed on the incident light side, and a lens 22 and a dichroic mirror 23 are disposed on the reflected light side. Also, an illuminating optical system, not shown, is arranged on the light beam incidence side onto the vibrating mirror 21 (the lower side as viewed in FIG. 5), and a light receiving optical system is arranged on the light beam emergence side (the right side as viewed in FIG. 5). The direction of reflection of a dichroic mirror 23 is optically coupled to the vibrating mirror 21, and an anterior eye part observation system, not shown, is arranged in the direction of light beam transmission of the dichroic mirror 23.

The illuminating optical system in this case, as in the first embodiment, is comprised of a slit plate 7, a light source 8, etc., and the light receiving optical system is comprised of a variable power lens 9, a linear array sensor 11, etc. Also, the anterior eye part observation system includes a television camera 5, etc., the linear array sensor 11 is connected to a television monitor 12 through a signal processor 13, and the television camera 5 is directly connected to the television monitor 12.

With this construction, the beam of light emitted from the light source 8 passes through the slit S of the slit plate 7 and is reflected by the vibrating mirror 21, and is projected onto the cornea Ec in an oblique direction through the lens 20. The beam of light reflected in an oblique direction by the cornea Ec is transmitted through the lens 22, and is reflected by the dichroic mirror 23 and arrives at the vibrating mirror 21, and is reflected by the back of the vibrating mirror 21 and enters the light receiving optical system, and is received by the linear array sensor 11. The light from the anterior part of the eye is transmitted through the dichroic mirror 23 and enters the anterior eye part observation optical system.

Figure 6:
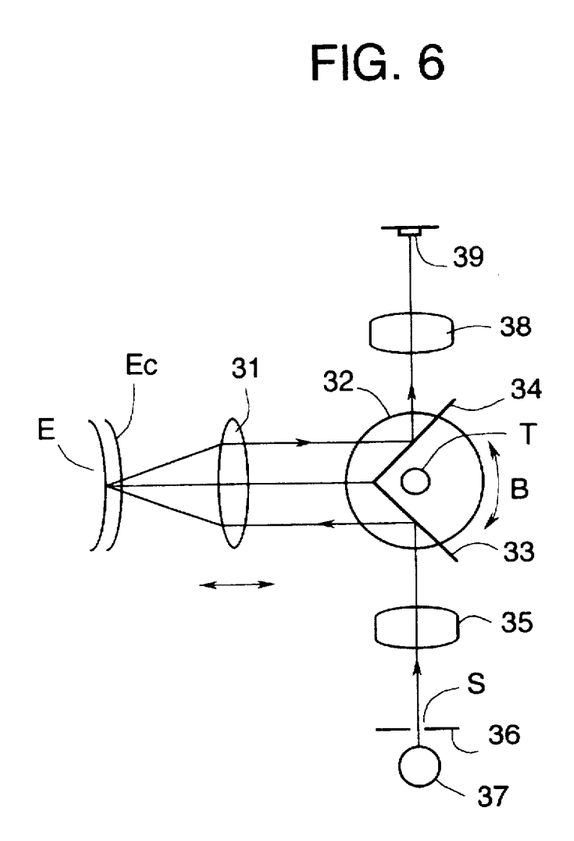
FIG. 6 shows the construction of a third embodiment of the present invention.

FIG. 6 shows the construction of an endothelium photographing apparatus according to a third embodiment of the present invention. This apparatus can also be used as a flare cell meter or a scattered light measuring apparatus for the crystalline lens and the vitreous body of an eye. An objective lens 31 and a vibrating member 32 are disposed ahead of the visual axis of the corner Ec of the eye E to be examined. Two mirrors 33 and 34 are fixed to the vibrating member 32, and these mirrors 33 and 34 are disposed line-symmetrically with respect to the optical axis with their ends made orthogonal to each other on the center of the optical axis. An illuminating optical system is arranged in a direction orthogonal to the optical axis of the objective lens 31 which is opposite to the mirror 33, and a light receiving optical system is arranged in a direction orthogonal to the optical axis of the objective lens 31 which is opposite to the mirror 34.

Figure 7:
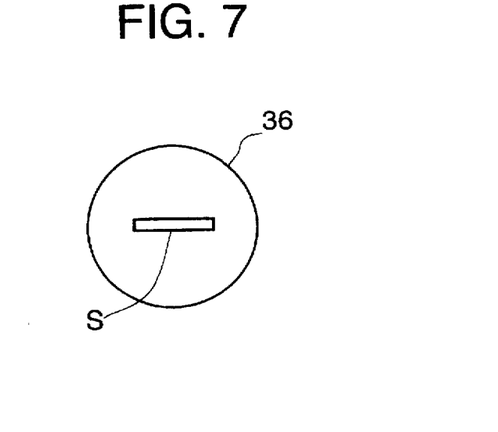
FIG. 7 is a front view of a slit plate.

The illuminating optical system comprises, in succession from the mirror 33, a lens 35, a slit 36 having a slit S as shown in FIG. 7, and a light source 37, and the light receiving optical system comprises, in succession from the mirror 34, a lens 38 and a linear array sensor 39 similar to that in FIG. 3. The linear array sensor 39 and the slit S of the slit plate 36 are in conjugate relationship with each other through the cornea Ec of the eye E to be examined, and one-dimensionally form a cofocal system.

The illuminating light emitted from the light source 37 becomes parallel light via the slit plate 36 and the lens 35, is reflected by the mirror 33, is transmitted through one side of the objective lens 31 and is projected onto the cornea Ec. In this case, the vibrating member 32 having the mirrors 33 and 34 fixed thereto vibrates in a direction B about a shaft T, like a galvanometric mirror, and therefore by the movement of the mirror 33, the illuminating slit light scans the cornea Ec. The reflected light from the cornea Ec is transmitted through the other side of the objective lens 31 and becomes parallel light, and is reflected by the mirror 34 and is imaged on the linear array sensor 39 such as a CCD through the lens 38.

As in the first embodiment, the signal of the linear array sensor 39 is processed by a signal processor and can be displayed as an image on a television monitor such as a CRT, or data likewise analyzed by the signal processor can be recorded in a printer or the like.

The objective lens 31 can be manually or electrically moved in the directions of a bilateral arrow on the optical axis shown in FIG. 7, whereby the beam of light can be condensed on the cornea Ec. For example, when used as a cell counter, the apparatus measures floating cells in the aqueous humor of the anterior chamber of the eye, and the objective lens 31 is operated with the vibrating member 32 and a predetermined volume in the aqueous humor of the anterior chamber of the eye is scanned to thereby count the number of cells in the predetermined volume. Likewise, scattered light in the vitreous body can be measured. Also, the objective lens 31 can be moved and images can be memorized at predetermined intervals, whereby a stereoscopic image can be formed by a computer.

When the working distance of the objective lens 31 cannot be secured sufficiently, the objective lens 31 is replaced with a lens of a greater focal length. Also, the lens 35 and the lens 38 can be moved on the optical axis in cooperative association with each other so that the slit S of the slit plate 36 and the linear array sensor 39 may always maintain their conjugate relationship, thereby effecting focusing.

Figure 8:
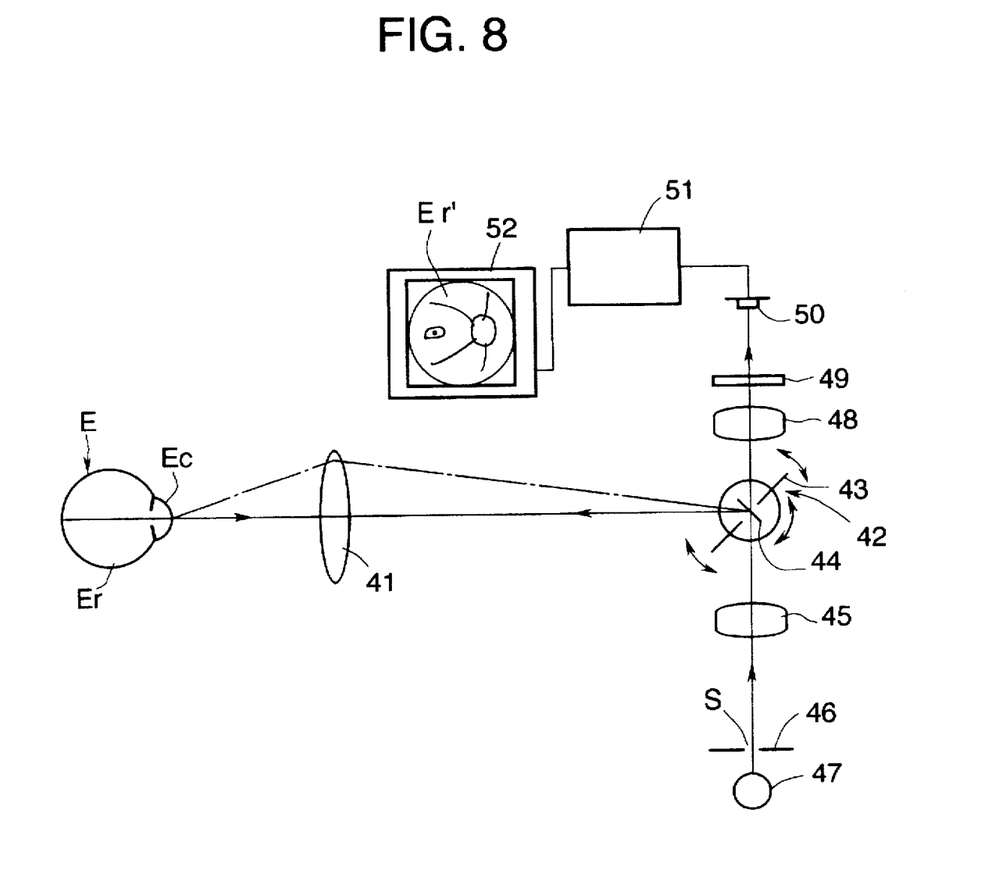
FIG. 8 shows the construction of a fourth embodiment of the present invention.
Figure 9:
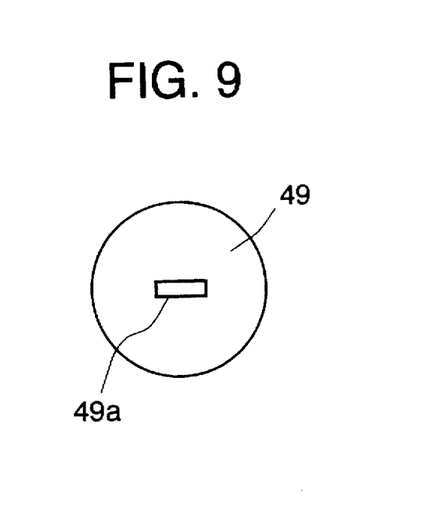
FIG. 9 is a front view of an apertured mirror.
Figure 10:
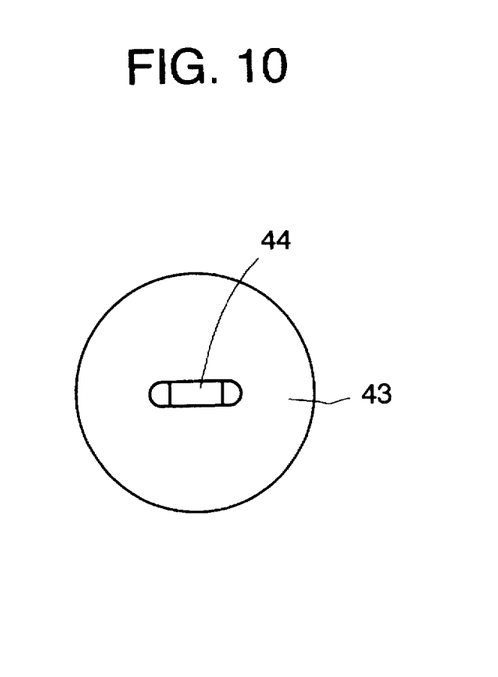
FIG. 10 is a front view of a light intercepting plate.

FIG. 8 shows an eye fundus observation apparatus according to a fourth embodiment of the present invention. An objective lens 41 and a vibrating member 42 are disposed ahead of the visual axis of the cornea Ec of the eye E to be examined. An apertured mirror 43 and a small mirror 44 are fixed to the vibrating member 42, and as shown in FIG. 10, the small mirror 44 is mounted in the aperture portion of the apertured mirror 43 at a location orthogonal to the apertured mirror 43. An illuminating optical system is arranged on the entrance side of the small mirror 44 and in a direction orthogonal to the optical axis of the objective lens 41, and a light receiving optical system is arranged on the opposite side of the apertured mirror 43 and in a direction orthogonal to the optical axis of the objective lens 41. A lens 45, a slit plate 46 and a light source 47 are disposed in the illuminating optical system in the named order, and a lens 48, a light intercepting plate 49 as shown in FIG. 10 and a linear array sensor 50 conjugate with the slit S of the slit plate 46 are disposed in the light receiving optical system in the named order. The output of the linear array sensor 50 is connected to a television monitor 52 through a signal processor 51.

A beam of light emitted from the light source 47 arrives at the slit S of the slit plate 46 and forms a slit image near the rear focus of the objective lens 41 by the lens 45 via the small mirror 44, but the vibrating member 42 vibrates in the directions of bilateral arrows shown in FIG. 8 about the optical axis of the small mirror 44, thereby slit-scanning the surface of the fundus of the eye. The reflected light from the fundus Er of the eye passes through the objective lens 41 and is reflected by the apertured mirror 43 which is likewise being vibrated by the vibrating member 42, and is imaged on the linear array sensor 50 via the lens 48 and the light intercepting plate 49. The signal of this linear array sensor displays an eye fundus image Er' on the television monitor 52 through the signal processor 51.

In this case, the angle formed between the apertured mirror 43 and the small mirror 44 does not necessarily need to be 90°. It is also possible to vary the measuring field in such a manner as to change the magnification of the lens 48 in cooperative association with the width of the slit S.

The light intercepting plate 49 is put into the illuminating optical system in an ordinary eye fundus camera, but in the present embodiment, the area of the beam of light on the light receiving side is, at the pupil, greater than that of the illuminating light and therefore, putting the light intercepting plate 49 into the light receiving optical system is more effective to eliminate the reflected light by the objective lens 41. Further, the light intercepting portion 49a of the light intercepting plate 49 is usually of the shape of a small black spot, but in the present embodiment, the apertured mirror 43 vibrates and therefore, the shape of the light intercepting portion 49a is linear.

Again in the present embodiment, as in the third embodiment, the lens 45 and the lens 48 are driven in cooperative association with each other to thereby effect focusing and effect similar measurement.

As described above, the eye examining apparatus according to the first or second embodiment is provided with a vibrating mirror and a reflecting member and adopts an anterior eye part observation system and a cofocal system, whereby it is simple in construction and can accomplish simple and accurate alignment by non-contact and obtain an enlarged image of good contrast.

Also, the eye examining apparatus according to the third or fourth embodiment adopts a dividing system for distributing the illuminating light and the received light by a set of vibrating mirrors provided on a vibratory member and a cofocal system, whereby it is simple in construction and can obtain an image of good contract, and an improvement in measurement accuracy, an improvement in images and the enlargement of the field of view become possible.

What is claimed is:

1. An eye examining apparatus comprising:
    a light source generating a beam of light to be applied to an eye to be examined;
    a photoelectric sensor for receiving the light from the eye to be examined, the examination of the eye to be examined being executed by the light reception of said photoelectric sensor;
    a scanning optical system for reflecting the beam of light to be applied from said light source to the eye to be examined and executing the scanning of the eye to be examined by said beam of light to be applied, and for reflecting the reflected light from the scanned position of the eye to be examined and for directing the reflected light from the scanned position to said photoelectric sensor; and
    an observation system for the eye to be examined for displaying an area wider than the scanned region of the eye to be examined by the use of the reflected light from the eye to be examined transmitted through a portion of a member of said scanning optical system.

2. The apparatus of claim 1, wherein said scanning optical system has a rotatable mirror.

3. The apparatus of claim 2, wherein said scanning optical system reflects the beam of light from said light source with a first reflecting surface of said rotatable mirror and applies the reflected beam of light to the eye to be examined and reflects the light from the scanned position of the eye to be examined with a second reflecting surface of said rotatable mirror and directs the reflected light from the eye to said photoelectric sensor.

4. The apparatus of claim 3, wherein said scanning optical system has a compound mirror for directing the light from the eye to be examined to the second reflecting surface of said rotatable mirror.

5. The apparatus of claim 4, wherein said observation system for the eye to be examined displays the eye to be examined by the use of the light transmitted through said compound mirror.

6. The apparatus of claim 3, wherein said scanning optical system has a dichroic mirror for directing the light from the eye to be examined to the second reflecting surface of said rotatable mirror.

7. The apparatus of claim 6, wherein said observation system for the eye to be examined displays the eye to be examined by the use of the light transmitted through said dichroic mirror.

8. The apparatus of claim 1, wherein the image signal of the scanned region of the eye to be examined is obtained by the light reception of said photoelectric sensor.

9. The apparatus of claim 8, wherein said scanning optical system has a variable power optical system between the eye to be examined to said photoelectric sensor.

10. The apparatus of claim 1, wherein said observation system for the eye to be examined displays the anterior eye part of the eye to be examined.

11. The apparatus of claim 1, wherein said scanning optical system has a slit in the optical path of the beam of light to be applied from said light source.

12. An eye examining apparatus comprising:
   a light source generating a beam of light to be applied to an eye to be examined;
   a photoelectric sensor for receiving the light from the eye to be examined, the examination of the eye to be examined being executed by the light reception of said photoelectric sensor; and
   a scanning optical system having a first mirror for deflecting the beam of light to be applied from said light source to the eye to be examined, and a second mirror for directing the light from the irradiated position of the eye to be examined by said beam of light to be applied to said photoelectric sensor, said first mirror and said second mirror being fixedly disposed to each other so that their reflecting surfaces are non-parallel to each other, and vibrating together with each other.

13. The apparatus of claim 12, wherein said first mirror and said second mirror are disposed so that their ends are orthogonal to each other.

14. An eye examining apparatus comprising:
   a light source generating a beam of light to be applied to an eye to be examined;
   a photoelectric sensor for receiving the light from the eye to be examined, the examination of the eye to be examined being executed by the light reception of said photoelectric sensor; and a scanning optical system having a first mirror for deflecting the beam of light to be applied from said light source to the eye to be examined, and a second mirror for directing the light from an irradiated position of the eye to be examined by said beam of light to be applied to said photoelectric sensor, said first mirror and said second mirror being fixedly disposed to each other so that their reflecting surfaces are non-parallel to each other, and vibrating together with each other,
   wherein said second mirror is an apertured mirror, and said first mirror is disposed in the aperture portion of said second mirror.

15. An eye examining apparatus comprising:
   a light source;
   a photoelectric sensor;
   a beam deflecting optical system for deflecting a beam from said light source to apply the beam to an eye to be examined, for changing a deflecting angle of the beam, and for guiding reflected light from the eye to said photoelectric sensor, eye examination being executed by the reception of the reflected light guided by said deflecting optical system by said photoelectric sensor, said beam deflecting optical system having a light dividing member; and
   an observation system for obtaining a two-dimensional image of the eye by way of said light dividing member.

* * * * *

UNITED STATES PATENT AND TRADEMARK OFFICE
CERTIFICATE OF CORRECTION

PATENT NO. : 5,757,463

DATED : May 26, 1998

INVENTOR : YOSHIMI KOHAYAKAWA

It is certified that error appears in the above-identified patent and that said Letters Patent is hereby corrected as shown below:

ON THE COVER PAGE, AT [57], ABSTRACT,
Line 15, "member" should read --member of--.

COLUMN 2,
Lines 8 and 28, "vibratory" should read --vibrating--.
Line 52, "anterior eye" should read --anterior--.
Line 53, "part," should read --part of the eye,--.

COLUMN 3,
Line 36, "vibratory" should read --vibrating--.

COLUMN 6,
Line 13, "vibratory"should read --vibrating--.

COLUMN 8,
Line 4, "and a scanning" should read --and ¶ a scanning--.

Signed and Sealed this

Twenty-fourth Day of August, 1999

Attest:

Q. TODD DICKINSON

*Attesting Officer*   *Acting Commissioner of Patents and Trademarks*